United States Patent
Choi et al.

(10) Patent No.: US 9,420,381 B2
(45) Date of Patent: Aug. 16, 2016

(54) MULTIMEDIA PLAYING APPARATUS AND METHOD FOR OUTPUTTING MODULATED SOUND ACCORDING TO HEARING CHARACTERISTIC OF USER

(71) Applicant: Samsung Electronics Co., Ltd., Suwon-si (KR)

(72) Inventors: Jong-min Choi, Seoul (KR); Dong-wook Kim, Seoul (KR); Jun-il Sohn, Yongin-si (KR); Yun-seo Ku, Seoul (KR); Jong-jin Kim, Hwaseong-si (KR); Sang-uk Bae, Hwaseong-si (KR); Jun-whon Uhm, Anyang-si (KR); Heun-chul Lee, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 250 days.

(21) Appl. No.: 13/740,798

(22) Filed: Jan. 14, 2013

(65) Prior Publication Data
US 2013/0182855 A1 Jul. 18, 2013

(30) Foreign Application Priority Data
Jan. 13, 2012 (KR) ........................ 10-2012-0004517

(51) Int. Cl.
*H04R 5/00* (2006.01)
*H04R 25/00* (2006.01)
*A61B 5/12* (2006.01)
*H04R 5/04* (2006.01)

(52) U.S. Cl.
CPC ............. *H04R 25/30* (2013.01); *A61B 5/121* (2013.01); *H04R 5/04* (2013.01); *H04R 2205/041* (2013.01); *H04R 2430/01* (2013.01); *H04R 2430/03* (2013.01); *H04R 2499/15* (2013.01)

(58) Field of Classification Search
None
See application file for complete search history.

(56) References Cited

U.S. PATENT DOCUMENTS

| 5,420,930 | A | * | 5/1995 | Shugart, III | 381/315 |
|---|---|---|---|---|---|
| 9,008,340 | B2 | | 4/2015 | Ku et al. | |
| 2008/0008070 | A1 | * | 1/2008 | Kwon | 369/53.1 |
| 2009/0268919 | A1 | * | 10/2009 | Arora | 381/56 |
| 2011/0046511 | A1 | * | 2/2011 | Koo et al. | 600/559 |
| 2011/0087130 | A1 | | 4/2011 | Cheema et al. | |
| 2011/0200215 | A1 | * | 8/2011 | Apfel et al. | 381/314 |
| 2012/0051553 | A1 | | 3/2012 | Sohn et al. | |

(Continued)

FOREIGN PATENT DOCUMENTS

| JP | 06-133953 A | 5/1994 |
|---|---|---|
| JP | 06-175817 A | 6/1994 |

(Continued)

*Primary Examiner* — Tan X Dinh
(74) *Attorney, Agent, or Firm* — NSIP Law (57) ABSTRACT

Multimedia playing apparatuses and methods of measuring hearing characteristics of a user and outputting a sound modulated according to the hearing characteristics of the user are provided. A multimedia playing apparatus includes a sound output unit configured to output a sound comprising of one or more phonemes, and a user interface configured to receive a user response to the phonemes. The multimedia playing apparatus further includes a processor configured to acquire hearing characteristics of a user based on the user response, and determine an output level and/or an output time of the sound for each of frequency bands based on the hearing characteristics of the user. The sound output unit is further configured to output the sound according to the output level and/or the output time of the sound for each of the frequency bands.

18 Claims, 7 Drawing Sheets

(56) References Cited

U.S. PATENT DOCUMENTS

| | | | |
|---|---|---|---|
| 2012/0070008 A1 | 3/2012 | Sohn et al. | |
| 2012/0197634 A1* | 8/2012 | Ishikawa et al. | 704/201 |
| 2013/0028428 A1* | 1/2013 | Katsumata | 381/56 |
| 2013/0343585 A1* | 12/2013 | Bennett et al. | 381/315 |

FOREIGN PATENT DOCUMENTS

| | | |
|---|---|---|
| JP | 09-038069 A | 2/1997 |
| JP | 2003-504646 A | 2/2003 |
| JP | 2003-102707 A | 4/2003 |
| KR | 1997-0020054 A | 5/1997 |
| KR | 1998-039701 A | 8/1998 |
| KR | 10-2000-0004049 A | 1/2000 |
| KR | 10-0707339 B1 | 4/2007 |
| KR | 10-2007-0099749 A | 10/2007 |
| KR | 10-0916726 B1 | 9/2009 |
| KR | 10-2010-0022880 A | 3/2010 |
| KR | 10-2011-0018829 A | 2/2011 |
| KR | 10-2012-0020527 A | 3/2012 |
| KR | 10-2012-0131778 A | 12/2012 |

* cited by examiner

MULTIMEDIA PLAYING APPARATUS AND METHOD FOR OUTPUTTING MODULATED SOUND ACCORDING TO HEARING CHARACTERISTIC OF USER

CROSS-REFERENCE TO RELATED APPLICATIONS

This application claims the benefit under 35 U.S.C. §119(a) of Korean Patent Application No. 10-2012-0004517, filed on Jan. 13, 2012, in the Korean Intellectual Property Office, the entire disclosure of which is incorporated herein by reference for all purposes.

BACKGROUND

1. Field

The following description relates to multimedia playing apparatuses and methods of measuring hearing characteristics of a user and outputting a sound modulated according to the hearing characteristics of the user.

2. Description of the Related Art

The number of people with hearing loss has increased due to the use of acoustic devices, the increase of noise, and the increase of aged people. Thus, those who have partial hearing loss and feel difficulty in hearing sounds of a frequency band, or those who have hearing loss in one ear, are also increasing in number.

People with hearing loss tend not to go to the hospital until their hearing loss have proceeded to make very large inconveniences in their everyday lives. Even if they go to the hospital and are diagnosed with hearing loss, such people are likely to live without using hearing aids due to psychological resistance and/or inconveniences in wearing the hearing aids.

SUMMARY

In one general aspect, there is provided a multimedia playing apparatus including a sound output unit configured to output a sound comprising of one or more phonemes, and a user interface configured to receive a user response to the sound. The multimedia playing apparatus further includes a processor configured to acquire hearing characteristics of a user based on the user response, and determine an output level and/or an output time of the sound for each of frequency bands based on the hearing characteristics of the user. The sound output unit is further configured to output the sound according to the output level and/or the output time of the sound for each of the frequency bands.

In another general aspect, there is provided a method of outputting a sound according to hearing characteristics of a user in a multimedia playing apparatus, the method including outputting a sound comprising of one or more phonemes, and receiving a user response to the phonemes. The method further includes acquiring the hearing characteristics of the user based on the user response, and determining an output level and/or an output time of the sound for each of frequency bands based on the hearing characteristics of the user. The method further includes outputting the sound according to the output level and/or the output time of the sound for each of the frequency bands.

Other features and aspects may be apparent from the following detailed description, the drawings, and the claims.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

Figure 1:
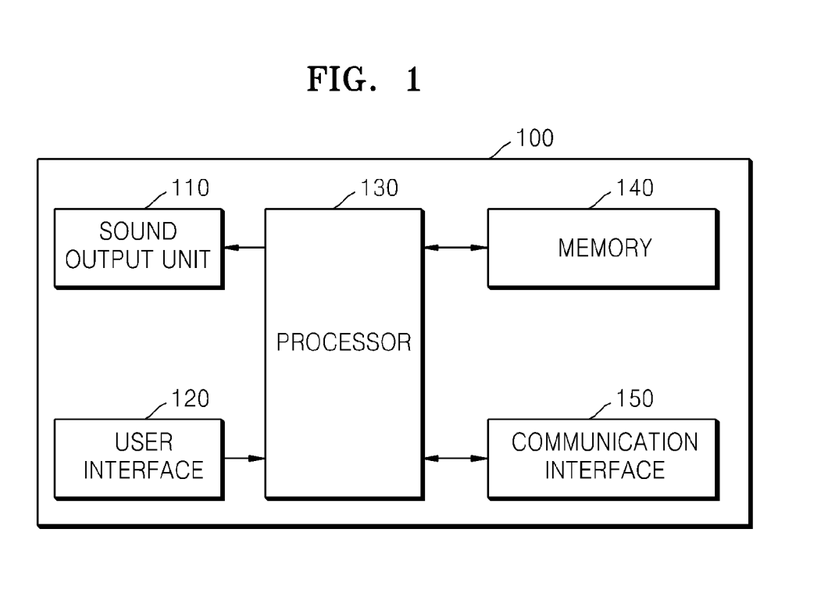
FIG. 1 is a block diagram illustrating an example of a multimedia playing apparatus.

FIG. 1 is a block diagram illustrating an example of a multimedia playing apparatus 100. Referring to FIG. 1, the multimedia playing apparatus 100 includes a sound output unit 110, a user interface 120, a processor 130, a memory 140, and a communication interface 150.

In FIG. 1, the multimedia playing apparatus 100 is illustrated to include only constituent elements related to the example, and to clarify technical features of the example. Therefore, those of ordinary skill in the art would understand that the multimedia playing apparatus 100 may further include general constituent elements, in addition to the components shown in FIG. 1.

The multimedia playing apparatus 100 may reproduce various media combining text, graphics, images, and/or sound. The multimedia playing apparatus 100 may be a television (TV), a personal computer (PC), a projector, a digital versatile disk (DVD) player, a video game machine, and/or other devices known to one of ordinary skill in the art.

The sound output unit 110 outputs a sound to acquire hearing characteristics of a user. The hearing characteristics of the user represent a minimum intensity (hereinafter, a hearing threshold) of the sound that the user may hear for each frequency band. Accordingly, the sound output unit 110 may output a sound of one frequency band repeatedly with various intensities, and may repeatedly perform this operation with respect to each other frequency band. For example, the sound output unit 110 may output a sound, such as a clicking sound, a tone pip, or a tone burst sound, of a single frequency.

An example of outputting the clicking sound will be described. The sound output unit 110 may repeatedly output the clicking sound of a constant frequency of about 1 kHz while gradually increasing or decreasing an intensity of the clicking sound. The output unit 110 may also repeatedly output the clicking sound of each frequency other than 1 kHz while adjusting an intensity of the clicking sound.

Based on the output sound, the multimedia playing apparatus 100 acquires the hearing characteristics of the user. The hearing characteristics of the user represent the hearing threshold of the user for each frequency band.

The sound output unit 110 may output a sound including at least one phoneme. A phoneme is a minimal unit of sound that serves to distinguish meaning of a language, and examples of the phoneme may include /ㄱ/, /ㄲ/, /ㅋ/, /ㅏ/, and /ㅗ/ in the Korean language, and /g/, /k/, /a/, and /o/ in the English language.

Phonemes may be classified in frequency bands according to a frequency characteristic of each of the phonemes. Therefore, the multimedia playing apparatus 100 may output sounds of phonemes, and may acquire the hearing threshold of the user for each of the phonemes. That is, the multimedia playing apparatus 100 may acquire the hearing threshold for each of frequency bands corresponding to the phonemes, thereby acquiring the hearing characteristics of the user.

The sound output unit 110 may output a sound of one phoneme repeatedly with various intensities, and may repeatedly perform this operation with respect to each other phoneme. For example, the sound output unit 110 may repeatedly output a sound of a phoneme /ㄴ/ in the Korean language while gradually increasing or decreasing an intensity of the sound. The sound output unit 110 may repeatedly output a sound of each phoneme besides the phoneme /ㄴ/ while adjusting an intensity of the sound. The phoneme /ㄴ/ corresponds to a frequency band ranging from about 250 Hz to about 500 Hz, according to its frequency characteristic. Accordingly, a hearing threshold of the phoneme /ㄴ/ corresponds to a hearing threshold of the frequency band ranging from about 250 Hz to about 500 Hz. The frequency bands corresponding to the phonemes will be described in detail with reference FIGS. 4 and 5.

Also, the sound output unit 110 may output a sound of a syllable or a word including one or more phonemes. One or more phonemes may combine with each other to form a syllable or a word. For example, phonemes /ㅎ/, /ㅣ/, and /ㅁ/ in the Korean language are combined to configure a syllable /힘/.

As described above, the phonemes may be classified in the frequency bands according to the frequency characteristic of each of the phonemes. Thus, the multimedia playing apparatus 100 may output the sound of the syllable or the word, and may acquire a hearing threshold of the user for the syllable or the word. That is, the multimedia playing apparatus 100 may acquire the hearing thresholds of for each of the frequency bands corresponding to the phonemes configuring the syllable or the word, thereby acquiring the hearing characteristics of the user.

The sound output unit 110 may output the sound of the syllable or the word including the phonemes repeatedly with various intensities. The sound output unit 110 may repeatedly perform this operation with respect to each other syllable or word including other phonemes.

Accordingly, the multimedia playing apparatus 100 may output a sound including one or more phonemes, such as a syllable or a word that the user is familiar with, to acquire or measure precise hearing characteristics of the user. Also, if the sound including the phonemes is output, sounds corresponding to different frequency bands may not be repeatedly output, and thus, a time taken to acquire the hearing characteristics of the user may be reduced.

The syllable or the word output from the sound output unit 110 may include phonemes that include similar sound pressures to each other. For convenience of description, such a syllable or word will be referred to as a phonetically-balanced word. In the phonetically-balanced word, the phonemes are overall balanced due to similar sound pressures to each other.

If a sound of a phonetically-balanced word is output to acquire hearing characteristics of the user, the hearing characteristics of the user may be acquired easily and rapidly. Phonetically-balanced words will be described in more detail with reference to FIG. 6.

The sound used to acquire the hearing characteristics of the user that is output from the sound output unit 110 is not limited to the above-described examples. In addition, the sound output unit 110 may include acoustic devices, such as a speaker, and/or a sound card that drives the acoustic devices.

The user interface 120 receives a user response to the sound output from the sound output unit 110. In more detail, the user listens to the sound output from the sound output unit 110, and inputs the user response to the sound in the user interface 120.

The user interface 120 may receive the user response representing whether the user hears the output sound. For example, the sound output unit 110 may output the clicking sound of about 1 kHz with an intensity of about 20 dB, and the user may input the user response representing whether the user hears the output clicking sound by using a button disposed in the user interface 120. Accordingly, the user interface 120 may receive the user response representing whether the user hears the output clicking sound of about 1 kHz with the intensity of about 20 dB.

The user interface 120 may receive the user response representing a sound that the user actually recognizes via text input or selection from a list in the user interface 120. For example, the sound output unit 110 may output the phoneme /ㄴ/ in the Korean language with an intensity of about 20 dB, and the user may select an actually recognized sound by using the button disposed in the user interface 120. Accordingly, the user interface 120 may receive the user response representing the actually recognized sound with respect to the output phoneme /ㄴ/ with the intensity of about 20 dB.

The manner that the user interface 120 receives the user response is not limited to the above-described examples. The user interface 120 may receive the user response in various manners.

The user interface 120 may include devices, such as a mouse, a keyboard, a touch pad, and/or a remote controller. However, the example of FIG. 1 is not limited thereto, that is, the user interface 120 may include any device that may receive the user response through pushing of a button, touching of a screen, and/or other methods known to one of ordinary skill in the art.

The processor 130 acquires the hearing characteristics of the user based on the user response, and determines an output level and/or an output time of the sound output from the sound output unit 110 for each frequency band based on the acquired hearing characteristics. As described above, the hearing characteristics of the user represent the hearing threshold of the user for each frequency band.

In more detail, after a sound of a frequency band is repeatedly output at various intensities, and the user response with respect to the sound is received, the processor 130 acquires the hearing threshold of the user for the corresponding frequency band. Also, the processor 130 acquires the hearing threshold of the user for each frequency band repeatedly to acquire the hearing characteristics of the user. As described above, the processor 130 acquires the hearing characteristics of the user based on the user response to the sound output from the sound output unit 110.

The processor 130 determines whether the user has a normal hearing ability based on the acquired hearing characteristics of the user, and if not, the processor 130 determines frequency bands the user has hearing loss, and to which extent a hearing ability of the user is damaged, based on the acquired hearing characteristics of the user. In more detail, the processor 130 determines each frequency band including the hearing threshold exceeding a predetermined permissible range, and calculates a hearing loss level of each determined frequency band. The predetermined permissible range denotes a medical reference range used to determine a normality of a hearing ability.

The processor 130 determines that there is a hearing loss of the user at each frequency band including the hearing threshold exceeding the predetermined permissible range, and calculates the hearing loss level of each frequency band determined to include the hearing loss. The hearing loss level may denote a difference between the hearing threshold of the user and a hearing threshold of the normal hearing ability, for the corresponding frequency band. Accordingly, the processor 130 calculates the hearing loss level of each frequency band in which there is the hearing loss, and determines an output level of the sound output from the sound output unit 110 for each frequency band based on the calculated hearing loss level.

The multimedia playing apparatus 100 outputs the sound modulated according to the determined output level for each frequency band through the sound output unit 110, and thus, outputs the sound in which the hearing loss of the user is compensated for. Accordingly, the user using the multimedia playing apparatus 100 hears the sound compensated for according to the hearing characteristics of the user.

The output level of the sound output from the sound output unit 110 for each frequency band denotes a degree of amplification amplifying a sound of the multimedia reproduced by the multimedia playing apparatus 100. Accordingly, the processor 130 determines an amplification level for each frequency band. For example, if it is determined that there is the hearing loss of the user in a high frequency band according to the hearing characteristics of the user, the processor 130 may determine the output level to amplify the sound of only the high frequency band. Accordingly, the multimedia playing apparatus 100 may reproduce the sound of the multimedia after adjusting the output level of the sound of each frequency band in which there is the hearing loss based on the hearing characteristics of the user.

For example, a user may not hear a sound of a frequency band due to aging and/or other conditions. In this example, the multimedia playing apparatus 100 may acquire hearing characteristics of the user, and may determine an output level of the sound based on the acquired hearing characteristics of the user, thereby outputting the sound modulated according to the hearing characteristics of the user when playing multimedia. Accordingly, the multimedia playing apparatus 100 may prevent further hearing loss of the user with respect to other frequency bands, in which a normal hearing ability has been maintained, that is caused by increasing a volume due to hard of hearing while playing the multimedia and by being continuously exposed to loud sound.

The processor 130 may include a digital signal processor (DSP) that processes digital signals. Accordingly, the processor 130 may perform digital signal processing, which may include dividing frequency bands of a digital signal into sections, amplifying and filtering the digital signal, and/or removing noise of the digital signal, thereby adjusting the sound accurately and finely. Also, the DSP of the processor 130 may amplify the sound non-linearly by adjusting a compression ratio, a knee point, an attack time, and/or a release time, for each frequency band.

The method of determining the output level of the sound output from the multimedia playing apparatus 100 based on the hearing characteristics of the user is not limited to the above description. That is, the output level may be determined according to various other methods that compensate for the hearing loss level of the user based on the hearing characteristics of the user.

The memory 140 stores the hearing characteristics of the user and the output level of the sound output from the multimedia playing apparatus 100, for each frequency band. The hearing characteristics of the user include the hearing threshold of the user for each frequency band, and the hearing threshold of each frequency band is acquired based on the user response input through the user interface 120. Accordingly, the memory 140 also stores the user response to the output sound, and the processor 130 acquires the hearing characteristics of the user based on the user response to the output sound, which is stored in the memory 140.

The output level of the sound output from the multimedia playing apparatus 100 for each frequency band is determined based on the hearing characteristics of the user that is stored in the memory 140. The memory 140 stores the determined output level for each frequency band, and the multimedia playing apparatus 100 reproduces the sound of the multimedia according to the output level for each frequency band, which is stored in the memory 140. That is, when the user uses the multimedia playing apparatus 100 to reproduce the multimedia, the processor 130 reads the output level for each frequency band of the user from the memory 140, and modulates the sound output via the sound output unit 110 based on the read output level.

Also, the memory 140 stores a history of hearing characteristics of each user. Accordingly, when the multimedia playing apparatus 100 acquires the hearing characteristics of the user, the hearing characteristics of the user being previously stored in the memory 140, the multimedia playing apparatus 100 outputs the sound to acquire the hearing characteristics of the user with reference to the history of the hearing characteristics of the user.

The processor 130 reads the hearing characteristics of the user that is stored in the memory 140. Accordingly, from the read hearing characteristics, the processor 130 acquires information representing whether there is the hearing loss of the user, each frequency band in which the user has hearing loss, and a degree of the hearing loss in each frequency band.

Accordingly, the processor 130 outputs the sound to acquire the hearing characteristics of the user based on the acquired information. For example, if the user has hearing loss in a high frequency band, the sound output unit 110 outputs the sound of only the high frequency band to acquire the hearing characteristics. Thus, the hearing characteristics about the sound of only the high frequency band that the user is interested in is acquired. Also, the sound output unit 110 outputs the sound with an intensity around the hearing loss level of the high frequency band where the user has hearing loss, thereby reducing a time taken to acquire the hearing characteristics.

By using the multimedia playing apparatus 100, the user may recognize easily whether the hearing loss of the user becomes worse, whether the hearing ability of the user is recovered after a surgery of a hearing organ, a proceeding degree of the hearing loss according to aging, and a proceeding degree of a sudden sensorineural hearing loss caused by sudden noise, with reference to the history of the hearing characteristics of the user that is stored in the memory 140. Additionally, the user may perform a hearing test easily, conveniently, and regularly.

Also, the memory 140 stores the sound to acquire the hearing characteristics of the user. As described above, the sound to acquire the hearing characteristics may include the clicking sound, the tone pip, the tone burst, and/or other sounds known to one of ordinary skill in the art that includes a constant frequency. Otherwise, the sound output unit 110 may output the sound including the phonemes to acquire the hearing characteristics.

The memory 140 may store information about the frequency bands corresponding to the phonemes. For example, the memory 140 may store one or more groups of the phonemes that are classified based on the frequency bands of the phonemes, and/or one or more groups of syllables including the phonemes that are classified based on the frequency bands of the phonemes.

The groups of the phonemes and the groups of the syllables include the phonemes and the syllables, respectively, corresponding to the frequency bands within an audible frequency range. The audible frequency range is a frequency range of a sound wave that may be heard by ears of a human being, which is a range from about 15 Hz to about 20 KHz. That is, the audible frequency range is classified into the frequency bands, and the syllables including the phonemes included in a classified frequency band may be grouped.

Also, the memory 140 may store groups of syllables including a list of the phonetically-balanced words, and a list of phonemes classified based on frequency characteristics of the phonemes.

The memory 140 may include a hard disk drive (HDD), a read only memory (ROM), a random access memory (RAM), a flash memory, and/or a memory card.

The communication interface 150 transmits/receives data via wired/wireless network or wired serial communication. The network may include the Internet, a local area network (LAN), a wireless LAN, a wide area network (WAN), and/or a personal area network (PAN). In addition, the communication interface 150 may perform communication through a universal serial bus (USB) memory.

The communication interface 150 receives the multimedia to be reproduced by the multimedia playing apparatus 100. The communication interface 150 may further transmit the acquired hearing characteristics of the user to an external device.

The multimedia playing apparatus 100 may further include an input/output interface (not shown). The input/output interface may connect the multimedia playing apparatus 100 to other sound output devices, to output the sound from the sound output unit 110 through the other sound output devices. For example, the input/output interface may connect the multimedia playing apparatus 100 to a head set and/or an earphone.

The multimedia playing apparatus 100 uses the sound output unit 110 including two or more channels to test a directivity of the user with respect to sound. A directivity test is a test that identifies whether the user recognizes a direction of the sound. Thus, the directivity test identifies whether the user distinguishes the direction from which the sound comes after outputting the sound toward the user from one or more locations surrounding the user.

In more detail, the sound output unit 110 outputs the sound via the two or more channels. The sound of each of the channels is output toward the user from one or more locations surrounding the user. Accordingly, the user may hear the sound output from one or more directions, and may recognize the directions of the sound.

The user may select and/or input the recognized directions of the sound via the user interface 120. For example, the user may select the recognized directions of the sound by using direction keys disposed in the user interface 120. In another example, the multimedia playing apparatus 100 may display numbers representing one or more output directions of the sound to the user via a display device (not shown), and the user may select at least one of the displayed numbers on the display device via the user interface 120 to input the recognized directions of the sound. However, the multimedia playing apparatus 100 is not limited to the above examples, and the user interface 120 may receive the recognized directions of the sound in various manners.

The processor 130 compares the directions of the sound output via the sound output unit 110 with the directions of the sound input via the user interface 120. That is, the processor 130 compares the directions of the sound output through the sound output unit 110 with the directions of the sound recognized by the user. The processor 130 tests the directivity of the user based on a result of the comparison.

The processor 130 determines the directivity according to a time difference of the sound. If the user does not recognize the directions in which the sound is output, the processor 130 adjusts the output time difference of the sound output through the sound output unit 110 to compensate for an ability of the user to recognize the directivity of the sound. In other words, the processor 130 determines the output time difference for each frequency band between the channels of the sound output unit 110 based on a result of the directivity test.

As described above, the multimedia playing apparatus 100 tests the directivity of the hearing ability of the user. Detailed descriptions thereof will be provided with reference to FIG. 8.

Figure 2:
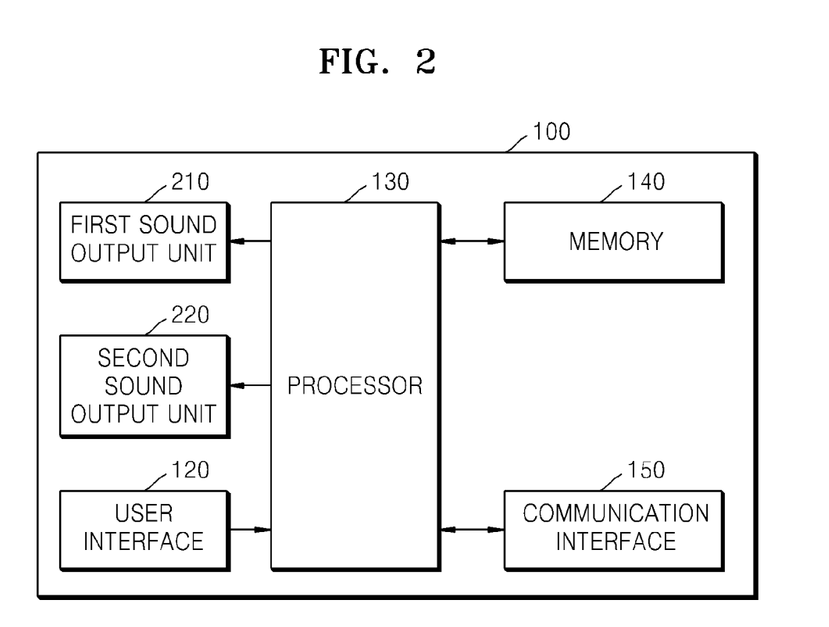
FIG. 2 is a block diagram illustrating another example of a multimedia playing apparatus.

FIG. 2 is a block diagram illustrating another example of the multimedia playing apparatus 100. Referring to FIG. 2, the multimedia playing apparatus 100 includes a first sound output unit 210, a second sound output unit 220, the user interface 120, the processor 130, the memory 140, and the communication interface 150.

The user interface 120, the processor 130, the memory 140, and the communication interface 150 shown in FIG. 2 are the same as those of FIG. 1, and thus, descriptions thereof are not repeated here. The multimedia playing apparatus 100 is not limited to the units shown in FIG. 2.

The multimedia playing apparatus 100 outputs a sound via two or more channels. The two or more channels may be realized as two or more sound output units corresponding to a number of the channels.

Hereinafter, for convenience of description, it is assumed that the multimedia playing apparatus 100 outputs the sound via two channels. Accordingly, the sound is output from each of the first sound output unit 210 and the second sound output unit 220, and the first and second sound output units 210 and 220 output the sound to right and left directions, respectively, of the user.

The first sound output unit 210 outputs the sound to acquire hearing characteristics of a right ear of the user. For example, the first sound output unit 210 may output the sound of a single frequency, e.g., a clicking sound, a tone pip, a tone burst, and/or other sounds known to one of ordinary skill in the art, repeatedly with various intensities. The first sound output unit 210 may also output the sound of each other frequency band repeatedly while changing an intensity of the sound. Accordingly, the multimedia playing apparatus 100 acquires the hearing characteristics of the right ear of the user via the first sound output unit 210.

Also, the first sound output unit 210 may output the sound including one or more phonemes repeatedly with various intensities. The first sound output unit 210 may also output the sound including one or more other phonemes corresponding to different frequency bands, repeatedly while changing an intensity of the sound. Accordingly, the multimedia playing apparatus 100 acquires the hearing characteristics of the right ear of the user, which represents a hearing threshold of the right ear of the user for each frequency band, through the first sound output unit 210. The sound including the phonemes that is output from the first sound output unit 210 may be realized as a syllable or a word.

The second sound output unit 220 outputs the sound to acquire hearing characteristics of a left ear of the user. For example, the second sound output unit 220 may output the sound of a single frequency repeatedly with various intensities while changing the frequency, and/or may output the sound including one or more phonemes, one or more syllables, or one or more words, repeatedly with various intensities, like the first sound output unit 210 described above.

The multimedia playing apparatus 100 acquires the accurate hearing characteristics of one ear (e.g., the right or left ear) of the user by blocking the sound output to the other ear while acquiring the hearing characteristics of the one ear. For example, while the multimedia playing apparatus 100 outputs the sound through the first sound output unit 210 to acquire the hearing characteristics of the right ear of the user, the multimedia playing apparatus 100 blocks the sound output to the left ear of the user so that the user may hear the sound output from the first sound output unit 210 through only the right ear.

The blocking is performed to prevent the hearing characteristics of one ear of the user from affecting the hearing characteristics of the other ear of the user, when there is a difference between hearing abilities of both ears of the user. Thus, the hearing characteristics of each ear of the user may be acquired accurately.

For example, when the multimedia playing apparatus 100 measures hearing characteristics of one ear of the user, which indicates a hearing loss greater than that of the other ear, the user may hear the sound output from the first sound output unit 210 (or the second sound output unit 220) via the other ear without hearing loss or including a small amount of hearing loss, thereby affecting the hearing characteristics of the one ear including the greater hearing loss. Accordingly, the hearing characteristics of the one ear that indicate the greater hearing loss, may show less hearing loss than an actual status of the one ear.

As described above, when determining an output level of the sound of each of the first sound output unit 210 and the second output unit 220 based on hearing characteristics with low precision, the multimedia playing apparatus 100 could not compensate for a hearing loss of the user. Therefore, when the multimedia playing apparatus 100 acquires the hearing characteristics of each ear of the user, the multimedia playing apparatus 100 acquires the precise hearing characteristics of each ear of the user by making the user hear only the sound output from the first sound output unit 210 (or the second sound output unit 220) via the one ear while blocking the sound output to the other ear.

The multimedia playing apparatus 100 may block the sound output to the other ear by using a headset or an earphone, or by outputting noise to the other ear including no or less hearing loss than the one ear. However, the example of FIG. 2 is not limited thereto, and one of ordinary skill in the art would appreciate that there are many ways to block a sound output to an ear.

Also, the multimedia playing apparatus 100 receives, from the user, a relative sound intensity of each ear after outputting the sound of different intensities from each of the first sound output unit 210 and the second sound output unit 220. Based on the received relative sound intensity of each ear, the multimedia playing apparatus 100 acquires the respective hearing characteristics of the right and left ears of the user.

For example, if the user responds that the sound heard by one ear is greater than the sound heard by the other ear with respect to the sounds of the same intensity output from the first and second sound output units 210 and 220, respectively, the multimedia playing apparatus 100 makes each of the first sound output unit 210 and the second sound output unit 220 output the sound of different intensities to receive the user response about the relative sound intensity of each ear. That is, the multimedia playing apparatus 100 adjusts an intensity of the sound output from each of the first and second sound output units 210 and 220 to receive, from the user, the relative sound intensity heard by each ear. Then, the multimedia playing apparatus 100 acquires a relative hearing threshold of each ear based on the received relative sound intensity. The multimedia playing apparatus 100 acquires relative hearing characteristics of each ear of the user based on the relative hearing threshold of the corresponding ear for each frequency band.

The multimedia playing apparatus 100 may store the respective hearing characteristics of the right and left ears of the user, which are previously measured, in the memory 140, or may receive the respective hearing characteristics through the communication interface 150. The multimedia playing apparatus 100 acquires the respective hearing characteristics of both ears based on the acquired relative hearing characteristics of both ears.

The multimedia playing apparatus 100 determines a relative output level of the sound output from each of the first and second sound output units 210 and 220 based on the relative hearing characteristics of both ears of the user. Thus, the multimedia playing apparatus 100 outputs the sound compensating for the hearing loss of both ears of the user.

The user interface 120 receives the user response to the sound output from each of the first sound output unit 210 and the second sound output unit 220. In more detail, the multimedia playing apparatus 100 receives the user response to the sound output from the first sound output unit 210 through the user interface 120, and acquires the hearing characteristics of the right ear of the user, which represent the hearing threshold of the right ear for each frequency band, based on the user response. Also, the multimedia playing apparatus 100 receives the user response to the sound output from the second sound output unit 220 through the user interface 120, and acquires the hearing characteristics of the left ear of the user, which represent the hearing threshold of the left ear for each frequency band, based on the user response.

The user interface 120, as shown with reference to FIG. 1, may receive the user response representing a sound that the user actually recognizes in response to the sound output from each of the first and second sound output units 210 and 220, via text input and/or selection from a list. Also, the user interface 120 may receive, from the user, the relative intensity of the sound output from each of the first and second sound output units 210 and 220. However, the example of FIG. 2 is not limited thereto, and the user interface 120 may receive the user response in various other manners.

The user interface 120 may further include a sound level meter that measures a sound pressure of the sound output from each of the first sound output unit 210 or the second sound output unit 220. In order to acquire the accurate hearing characteristics of the user by using the multimedia playing apparatus 100, a method of identifying whether an intensity of a sound set by the multimedia playing apparatus 100 is equal to the intensity of the sound actually output from each of the first or second sound output unit 210 or 220, and a calibration method are needed. Accordingly, the user interface 120 includes the sound level meter to measure the intensity of the sound output from each of the first or second sound output unit 210 or 220, and the processor 130 calibrates the intensity of the sound output from each of the first or second sound output unit 210 or 220 based on the measured intensity. Thus, even if the output intensity of the system that is used to test the hearing characteristics is changed due to time elapse or other external elements, the multimedia playing apparatus 100 calibrates the system to test the hearing characteristics easily by using the sound level meter included in the user interface 120. Also, the user may regularly calibrate the system to test the hearing characteristics by using the sound level meter included in the user interface 120.

The processor 130 determines an output level of the sound for each frequency band with respect to each channel based on the respective hearing characteristics of the right ear and the left ear of the user. In more detail, the processor 130 determines the output level of the sound for each frequency band with respect to each channel based on a difference between the hearing characteristics of both ears, and then, outputs the sounds that compensate for the hearing loss of the user having the different hearing loss levels in both ears.

In more detail, the processor 130 determines an output level difference and an output time difference between the channels for each frequency band based on the respective hearing characteristics of the right and left ears of the user. That is, the processor 130 outputs the sound through the first sound output unit 210, and acquires the hearing characteristics of the right ear of the user based on the user response to the output sound. The processor 130 determines the frequency band in which the hearing threshold of the right ear of the user exceeds a predetermined permissible range, based on the acquired hearing characteristics of the right ear. The frequency band in which the hearing threshold of the right ear exceeds the predetermined permissible range, is a frequency band including the hearing loss of the right ear. The processor 130 calculates a hearing loss level of the right ear in the determined frequency band including the hearing loss, which represents a difference between the hearing threshold of the right ear and a hearing threshold of a normal hearing ability with respect to the determined frequency band including the hearing loss.

Also, the processor 130 outputs the sound through the second sound output unit 220, and acquires the hearing characteristics of the left ear of the user based on the user response to the output sound. The processor 130 determines the frequency band including the hearing loss of the left ear, and calculates a hearing loss level of the left ear in the determined frequency band.

The processor 130 compares the respective hearing characteristics of the right ear and the left ear of the user with each other. In more detail, the processor 130 compares the hearing loss levels of the right ear and the left ear in the same frequency band, with each other. Accordingly, the processor 130 determines the output level difference and the output time difference between the channels based on a result of the comparison, and accordingly, determines the output levels of each frequency band with respect to each channel.

For example, if the frequency band determined to include the hearing loss is a low frequency band, the processor 130 determines the output levels of each frequency band with respect to each channel by increasing the output level difference between the channels for a high frequency component. The processor 130 may increase the output level difference between the channels for the high frequency component by increasing sound pressures for high frequency bands. Also, if the frequency band determined to include the hearing loss is a high frequency band, the processor 130 determines the output levels of each frequency band with respect to each channel by increasing the output time difference between the channels for a low frequency component.

In more detail, if the user has hearing loss in the low frequency band according to the hearing characteristics of the user, the processor 130 increases the output level difference between the output level of the high frequency component output from the first sound output unit 210 and the output level of the high frequency component output from the second sound output unit 220. Accordingly, the multimedia playing apparatus 100 compensates for the hearing loss in the low frequency band of the user. For example, if there is an output level difference of about 1 dBSPL between the output level of the high frequency component output from the first sound output unit 210 and the output level of the high frequency component output from the second sound output unit 220, the processor 130 may increase the output level difference between the output levels of the high frequency components output from the first and second sound output units 210 and 220 to 2 dBSPL.

Also, if the user has hearing loss in the high frequency band according to the hearing characteristics of the user, the processor 130 increases the output time difference between an output time of the low frequency component output from the first sound output unit 210 and an output time of the low frequency component output from the second sound output unit 220. Accordingly, the multimedia playing apparatus 100 compensates for the hearing loss in the high frequency band of the user. For example, if there is an output time difference of about 1 msec between the output time of the low frequency component output from the first sound output unit 210 and the output time of the low frequency component output from the second sound output unit 220, the processor 130 may increase the output time difference between the output times of the low frequency components output from the first and second sound output units 210 and 220 to 2 msec.

As described above, the processor 130 increases the output level difference between the channels, or the output time difference between the channels, in order to compensate for the hearing loss according to whether the frequency band including the hearing loss is the low frequency band or the high frequency band. This is because frequency dependencies of an inter-aural level difference (ILD) and an inter-aural time difference (ITD) vary depending on the frequency band. For example, the frequency dependency of the ILD is high at the high frequency band, and is not high at the low frequency band. Also, the frequency dependency of the ITD is high at the low frequency band, and is not high at the low frequency band. This will be described in more detail with reference to FIG. 3. Accordingly, the processor 130 determines the output level difference and the output time difference between the channels for each frequency band based on the frequency dependency of the ILD and the frequency dependency of the ITD, respectively, of each frequency band.

Therefore, each of the first and second sound output units 210 and 220 output the sound modulated according to the output level difference and the output time difference between the channels for each frequency band, which are determined by the processor 130.

Accordingly, the multimedia playing apparatus 100 outputs the sound that compensates for the hearing loss of the user who has the different hearing loss levels in both ears by determining the output level difference and the output time difference between the channels for each of frequency band. Therefore, the multimedia playing apparatus 100 outputs the appropriate sound that compensates for the hearing loss of the user according to the hearing characteristics of the user, thereby preventing an ear including normal hearing ability, or less hearing loss, from being worse.

The memory 140 stores the hearing characteristics of the right ear and the left ear of the user that are acquired by the processor 130. Also, the memory 140 stores the output level difference and the output time difference between the channels for each of frequency band, which are determined by the processor 130.

Also, the memory 140 stores the output level difference and the output time difference determined for each user. Accordingly, if the user uses the multimedia playing apparatus 100 to reproduce the multimedia at another time, the multimedia playing apparatus 100 outputs the sound suitable for the user by reading the determined output level difference and the output time difference for the user from the memory 140.

The memory 140 stores a history of the hearing characteristics of the right ear and left ear for each user. Accordingly, if the user uses the multimedia playing apparatus 100 to measure the hearing characteristics of the user at another time, the multimedia playing apparatus 100 reads the history of the hearing characteristics of the user, thereby reducing a time taken to test the hearing characteristics of the user.

The multimedia playing apparatus 100 reads the hearing characteristics of the user that are stored in the memory 140. From the read hearing characteristics, the multimedia playing apparatus 100 acquires information about whether the user has the hearing loss, the frequency band including the hearing loss, and a degree of the hearing loss in the frequency band.

The processor 130 may acquire the hearing characteristics of the user in only the frequency band including the hearing loss. Accordingly, the user may rapidly identify a progress of the hearing loss in the frequency band that the user is interested in.

Also, the processor 130 outputs the sound at an intensity around the hearing loss level of the user. Thus, a time taken to acquire the hearing characteristics of the user may be reduced.

The communication interface 150 transmits/receives data via the wired/wireless network or the wired serial communication as shown in FIG. 1. Accordingly, the communication interface 150 receives the multimedia to be reproduced by the multimedia playing apparatus 100, and may transmit/receive the hearing characteristics of the user to/from an external device.

The multimedia playing apparatus 100 determines the output level difference and the output time difference between the channels for each frequency band even if the user has the hearing loss in the corresponding frequency band, or degrees of the hearing loss in both ears are different from each other. Thus, various types of hearing loss may be compensated easily and rapidly.

Figure 3:
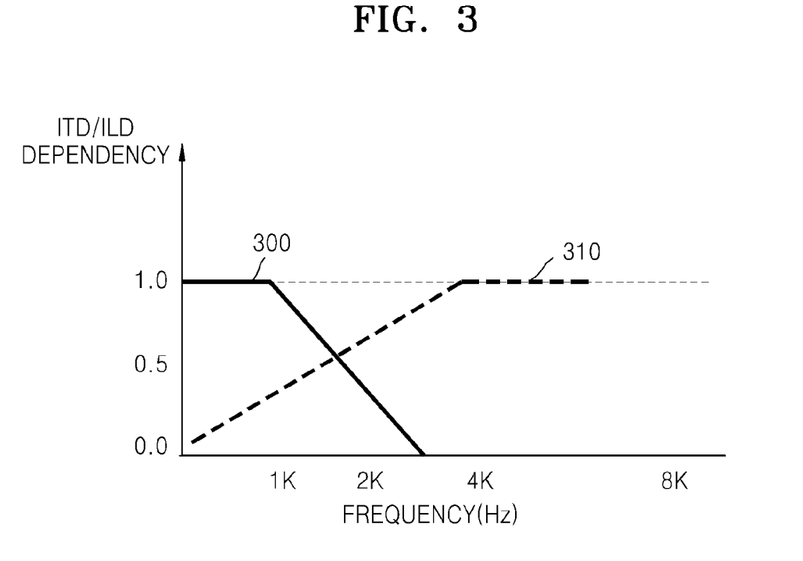
FIG. 3 is a graph illustrating an example of a frequency dependency of an interaural level difference, and an example of a frequency dependency of an interaural time difference.

FIG. 3 is a graph illustrating an example of a frequency dependency of an ILD 310, and an example of a frequency dependency of an ITD 300. In the graph of FIG. 3, a longitudinal axis denotes the frequency dependencies of the ILD and the ITD 310 and 300, and a transverse axis denotes a frequency (Hz). The frequency dependency of the ILD 310 is denoted by dotted lines, and the frequency dependency of the ITD 300 is denoted by a solid line.

Referring to FIG. 3, the frequency dependency of the ITD 300 gradually reduces as the frequency increases in a high frequency band. Accordingly, the ITD shows a high frequency dependency at a low frequency band of about 1.5 KHz or less, and a reduced frequency dependency at the high frequency band greater than about 1.5 kHz. This is because it is difficult to distinguish a difference of phases between channels at the high frequency band greater than 1.5 KHz.

The frequency dependency of the ILD 310 is low at a low frequency band, and gradually increases as the frequency increases in a high frequency band. The ILD shows a relatively low frequency dependency at the low frequency band less than about 3.5 kHz, and a high frequency dependency at the high frequency band of about 3.5 kHz or greater.

As described above, the frequency dependencies of the ITD and the ILD 300 and 310 vary depending on the frequency band. Accordingly, the multimedia playing apparatus 100 of FIG. 1 increases the ILD and/or the ITD between the channels in order to compensate for a hearing loss of a user, according to whether a frequency band including the hearing loss is a low frequency band or a high frequency band.

As described above, when the multimedia playing apparatus 100 compensates a difference between hearing losses in both ears of the user, the user may recognize a direction in which a sound comes from by using both ears. Also, the user may hear the modulated sound that compensates for the hearing losses in both ears, respectively. Thus, the user may recognize the sound at a low volume better than that recognized when the user hears the sound by using only one ear including a relatively superior hearing ability compared to the other ear.

Therefore, by using the multimedia playing apparatus 100, even if the user hears the sound in a noisy environment, the user may hear the sound with a balanced hearing ability between both ears, thereby improving a signal-to-noise ratio (SNR), word recognition, and speech discrimination. Accordingly, the multimedia playing apparatus 100 may prevent hearing loss of the ear with a normal hearing ability, and further hearing loss of the other ear including a hearing loss, caused if the user turns up the volume in order to hear the sound well in the noisy environment.

Figure 4:
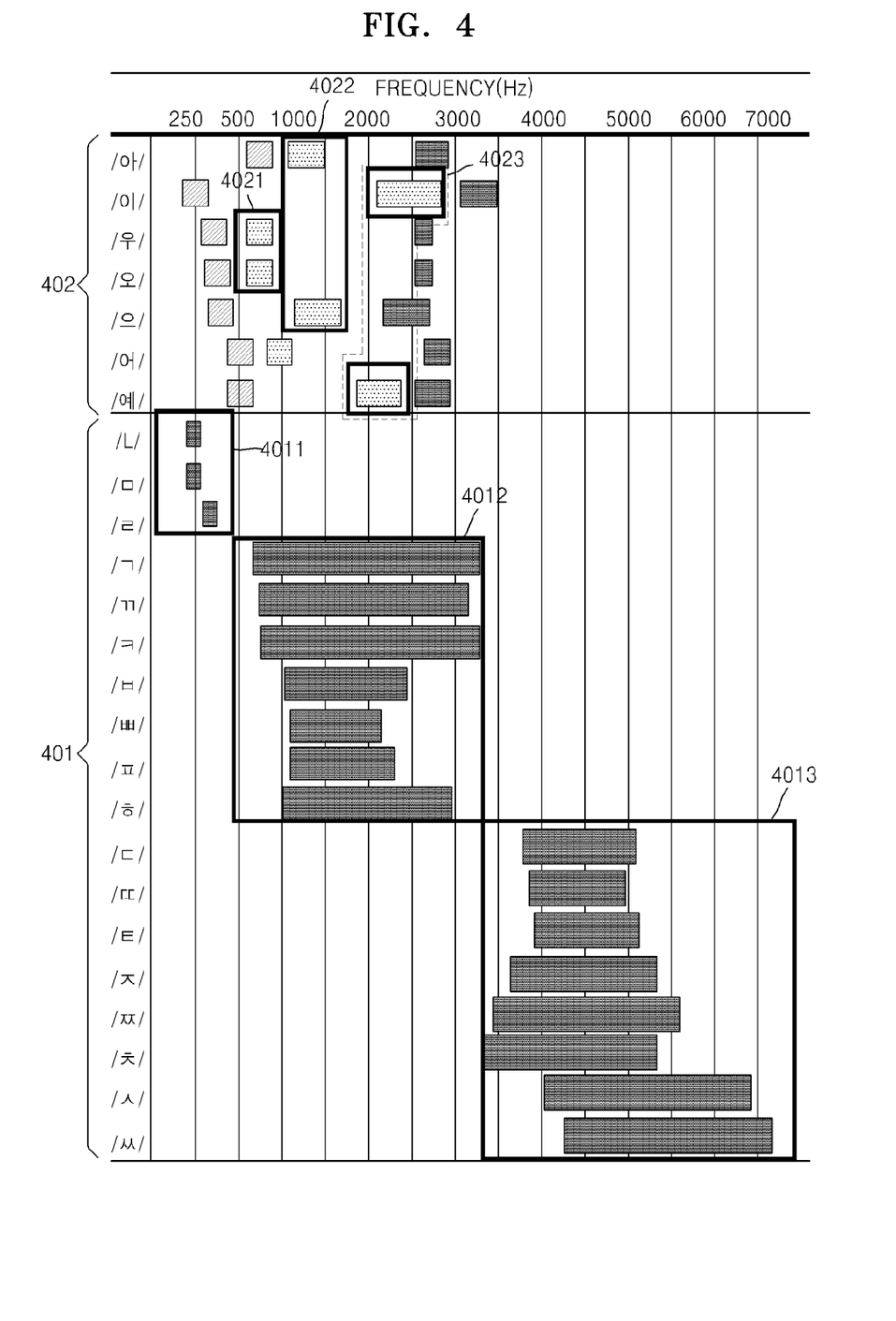
FIG. 4 is a diagram illustrating examples of frequency characteristics of phonemes of the Korean language.

FIG. 4 is a diagram illustrating examples of frequency characteristics of phonemes of the Korean language. Referring to FIG. 4, frequency ranges of the phonemes of the Korean language are classified into vowels and consonants. The vowels and the consonants are classified into a groups according to peak frequency ranges thereof.

In more detail, a consonant list 401 denotes frequency ranges of consonants classified into three groups according to their frequency ranges. Group 1 (4011) includes consonants included in a frequency range between about 250 Hz and less than about 500 Hz, Group 2 (4012) includes consonants included in a frequency range between about 650 Hz and less than about 3000 Hz, and Group 3 (4013) includes consonants included in a frequency range between about 3000 Hz and less than about 7000 Hz. Consonants such as /ㄴ/, /ㅁ/, and /ㅇ/ are included in Group 1 (4011), consonants such as /ㄱ/, /ㅋ/, /ㄹ/, /ㅂ/, /ㅃ/, /ㅍ/, and /ㅎ/ are included in Group 2 (4012), and consonants such as /ㄷ/, /ㄸ/, /ㅌ/, /ㅈ/, /ㅉ/, /ㅊ/, /ㅅ/, and /ㅆ/ are included in Group 3 (4013).

Also, a vowel list 402 denotes frequency ranges of vowels. Referring to the vowel list 402, each vowel corresponds to three formant frequencies. A formant frequency denotes a peak frequency showing a relatively high energy in a frequency spectrum that is obtained by integrating along a frequency axis according to an amplitude of a sound versus a time, of a vowel. Referring to the vowel list 402, three formant frequencies corresponding to each vowel may be indicated by, starting from a lowest frequency band, a first formant, a second formant, and a third formant, respectively. As shown in the vowel list 402, since frequency bands of first and third formants are similar across all vowels, vowels are classified into three groups based on frequency bands of second formants. According to the classification, vowels of a frequency range between about 600 Hz and less than about 800 Hz are included in Group 2-1 (4021), vowels of a frequency range between about 1000 Hz and less than about 1300 Hz are included in Group 2-2 (4022), and vowels of a frequency range between about 2000 Hz and less than about 3000 Hz are included in Group 2-3 (4023). In Group 2-1 (4021), vowels such as /어/ and /오/. are included, in Group 2-2 (4022), vowels such as /아/ and /우/ are included, and in Group 2-3 (4023), vowels such as /이/ and /에/ are included.

Referring to FIG. 4, in an example, after outputting sounds of one or more phonemes to a user, if audibility of the consonants of Group 3 (4013) is low, and the user cannot distinguish between the vowels /어/ and /아/ or between the vowels /오/ and /우/, it may be determined that the user has a hearing loss at the frequency range of Group 2-2 (4022) that is between about 1000 Hz and less than about 1300 Hz, and at the frequency range of Group 3 (4013) that is between about 2000 Hz and less than about 7000 Hz.

FIG. 4 shows the frequency characteristics of the phonemes of the Korean language. However, the frequency characteristics of the phonemes may also be applied to other languages.

Figure 5:
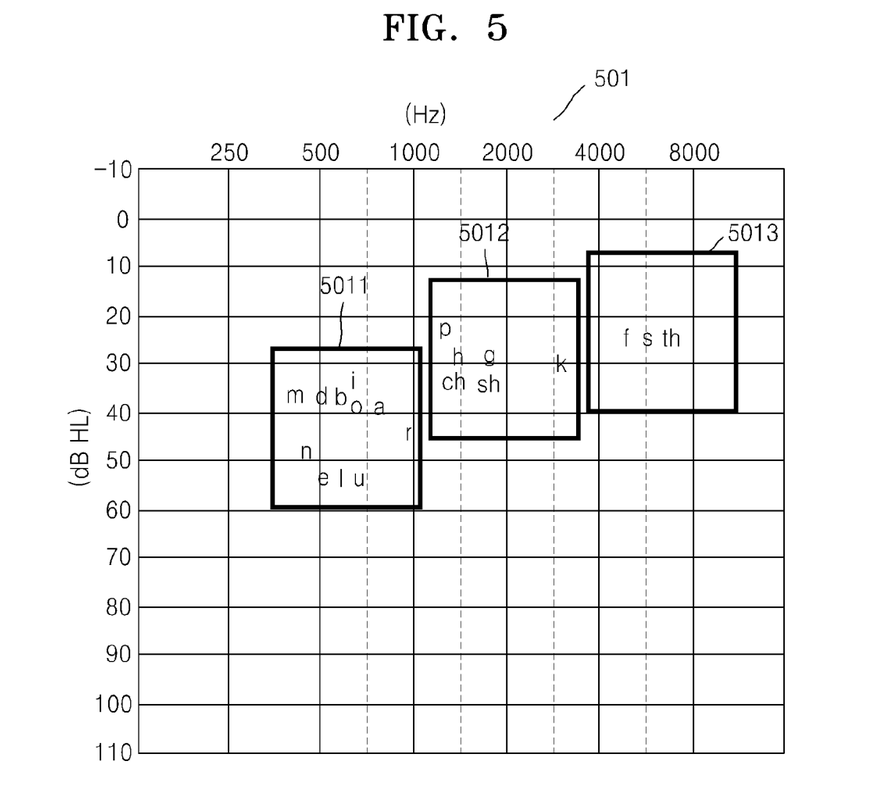
FIG. 5 is a diagram illustrating examples of frequency characteristics of phonemes of the English language.

FIG. 5 is a diagram illustrating examples of frequency characteristics of phonemes of the English language. Referring to FIG. 5, frequency ranges of the phonemes of the English language are shown, and the phonemes are classified into groups according to the frequency ranges thereof.

In more detail, a phoneme list 501 denotes frequency ranges of the phonemes classified into three groups according to their frequency ranges. Group 1 (5011) includes phonemes included in a frequency range between about 300 Hz and less than about 1200 Hz, Group 2 (5012) includes phonemes included in a frequency between about 1200 Hz and less than about 4000 Hz, and Group 3 (5013) includes phonemes included in a frequency range between about 4000 Hz and less than about 8000 Hz. Phonemes such as /m/, /d/, /b/, /i/, /o/, /a/, /n/, /e/, /l/. /u/, and /r/ are included in Group 1 (5011), phonemes such as /p/, /h/, /g/, /k/, /ch/, and /sh/ are included in Group 2 (5012), and phonemes such as /f/, /s/, and /th/ are included in Group 3 (5013).

The multimedia playing apparatus 100 of FIG. 1 may acquire hearing characteristics of a user with reference to the frequency characteristics of the phonemes of the Korean and English languages, respectively, shown in FIGS. 4 and 5. The memory 140 of FIG. 1 may store the groups of the phonemes, or groups of syllables, each including one or more of the phonemes classified based on their peak frequency ranges. The phonemes or the syllables forming the groups may be extracted from phonetically-balanced words.

Figure 6:
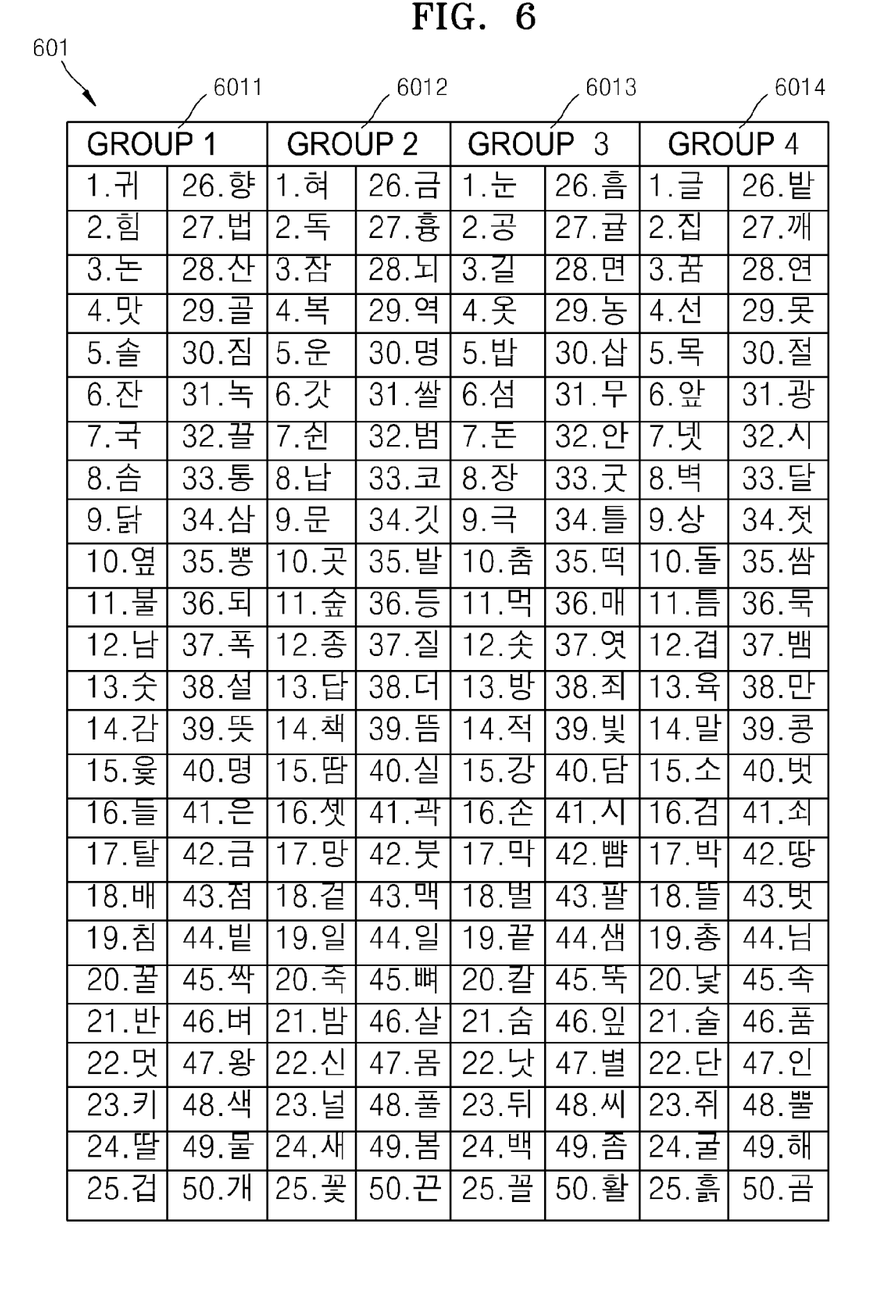
FIG. 6 is a diagram illustrating examples of phonetically-balanced words in the Korean language.

FIG. 6 is a diagram illustrating examples of phonetically-balanced words in the Korean language. Referring to FIG. 6, a phonetically-balanced word list 601 includes four groups, each including syllables including equivalent speech discrimination. The phonetically-balanced word list 601 includes Group 1 (6011), Group 2 (6012), Group 3 (6013), and Group 4 (6014), and each group includes monosyllables. The syllables including phonemes are balanced overall due to similar sound pressures generated when pronouncing the syllables. The phonetically-balanced word list 601 is only an example, and the multimedia playing apparatus 100 of FIG. 1 may acquire hearing characteristics of a user based on any other lists known to one of ordinary skill in the art that includes syllables including phonemes that are balanced overall due to similar sound pressures generated when pronouncing the syllables.

Figure 7:
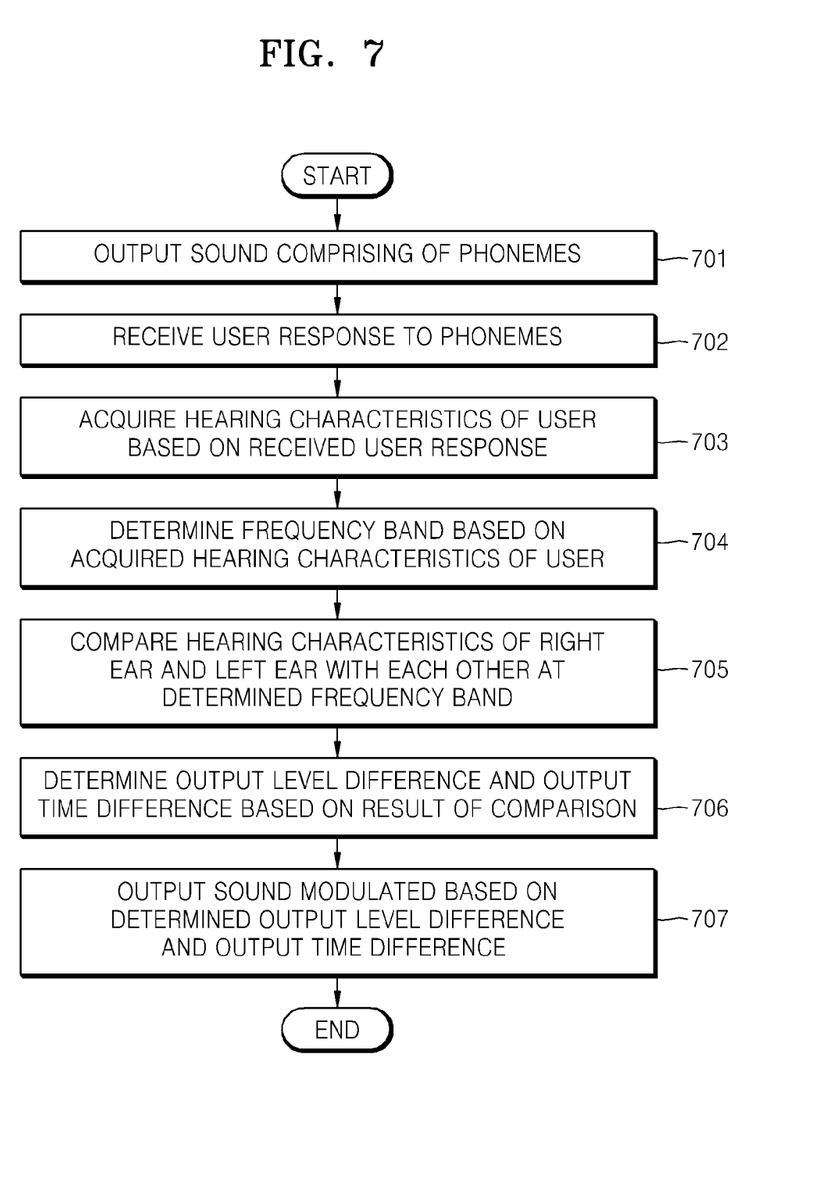
FIG. 7 is a flowchart illustrating an example of a method of outputting a sound modulated according to hearing characteristics of a user in a multimedia playing apparatus.

FIG. 7 is a flowchart illustrating an example of a method of outputting a sound modulated according to hearing characteristics of a user in a multimedia playing apparatus. Referring to FIG. 7, the method of outputting the sound modulated according to the hearing characteristics of the user includes the following operations that are performed in a time-serial manner in the multimedia playing apparatus 100 shown in FIGS. 1 and 2. Therefore, the components described above with reference to the multimedia playing apparatus 100 shown in FIGS. 1 and 2 may be applied to the method of outputting the sound modulated according to the hearing characteristics of the user of FIG. 7.

In operation 701, each of the first and second sound output units 210 and 220 outputs a sound to acquire the hearing characteristics of the user. In more detail, the first sound output unit 210 outputs the sound to acquire hearing characteristics of a right ear of the user, and the second sound output unit 220 outputs the sound to acquire hearing characteristics of a left ear of the user. For example, each of the first and second sound output units 210 and 220 may output the sound of a single frequency while changing intensities of the sound of the single frequency. Each of the first and second sound output units 210 and 220 may output sounds of other frequencies in the same manner. In another example, each of the first and second sound output units 210 and 220 may output the sound including one or more phonemes, syllables, and/or words, repeatedly with various intensities.

In operation 702, the user interface 120 receives, from the user, a user response to the output sound. In more detail, the user interface 120 receives, from the user, a user response to the sound output from the first sound output unit 210, and a user response to the sound output from the second sound output unit 220.

In operation 703, the processor 130 acquires the hearing characteristics of the user that represent a hearing threshold of the user for each frequency band based on the received user response. In more detail, the processor 130 acquires the hearing characteristics of the right ear of the user for respective frequency bands based on the user response to the sound output from the first sound output unit 210. Also, the processor 130 acquires the hearing characteristics of the left ear of the user for the respective frequency bands based on the user response to the sound output from the second sound output unit 220.

In operation 704, the processor 130 determines the frequency band including the hearing threshold exceeding a predetermined permissible range based on the acquired hearing characteristics of the user. In more detail, the processor 130 determines the frequency band including the hearing threshold exceeding the predetermined permissible range with respect to the right ear and the left ear of the user. The predetermined permissible range is a medical reference of determining a normal hearing ability. Accordingly, the frequency band including the hearing threshold exceeding the predetermined permissible range is a frequency range including a hearing loss of the user. As such, the processor 130 determines the frequency band including the hearing loss with respect to the right and left ears of the user.

In operation 705, the processor 130 compares the hearing characteristics of the right ear and the left ear with each other at the determined frequency band. In more detail, the processor 130 compares the hearing thresholds of the right and left ears with each other at the frequency band including the hearing loss of the user. For example, the processor 130 may calculate hearing loss levels of the right and left ears, respectively, at the frequency band including the hearing loss, and may compare the hearing loss levels of the right and left ears with each other to compare the hearing characteristics of the right and left ears with each other. The hearing loss level is a difference between the hearing threshold of a hearing ability (e.g., the right or left ear) of the user and a hearing threshold of the normal hearing ability.

In operation 706, the processor 130 determines an output level difference and an output time difference between channels based on a result of the comparison. For example, the processor 130 may determine the output level difference and the output time difference between the channels with reference to frequency dependencies of an ILD and an ITD, respectively. If the frequency band including the hearing loss of the user is a low frequency band, the processor 130 may increase the output level difference of a high frequency band between the channels. Otherwise, if the frequency band including the hearing loss of the user is the high frequency band, the processor 130 may increase the output time difference of the low frequency band between the channels.

In operation 707, each of the first and second sound output units 210 and 220 output the sound modulated based on the determined output level difference and the output time difference between the channels. Accordingly, the multimedia playing apparatus 100 measures the hearing characteristics of the user easily and rapidly. Also, the multimedia playing apparatus 100 outputs the sound that compensates for the hearing loss of the user based on the hearing characteristics of the user, and thus, the user may hear the sound without any inconvenience of an additional hearing aid.

The multimedia playing apparatus 100 stores hearing characteristics of a plurality of users, and output level differences and output time differences determined based on the hearing characteristics, and thus, the multimedia playing apparatus 100 outputs the sound modulated according to the hearing characteristics of the corresponding user. Even if the hearing loss levels of both ears of the user are different from each other, the multimedia playing apparatus 100 adjusts the output level difference and the output time difference of each frequency band between two or more channels, and thus, outputs the sound that compensates for the hearing loss of both ears appropriately.

Figure 8:
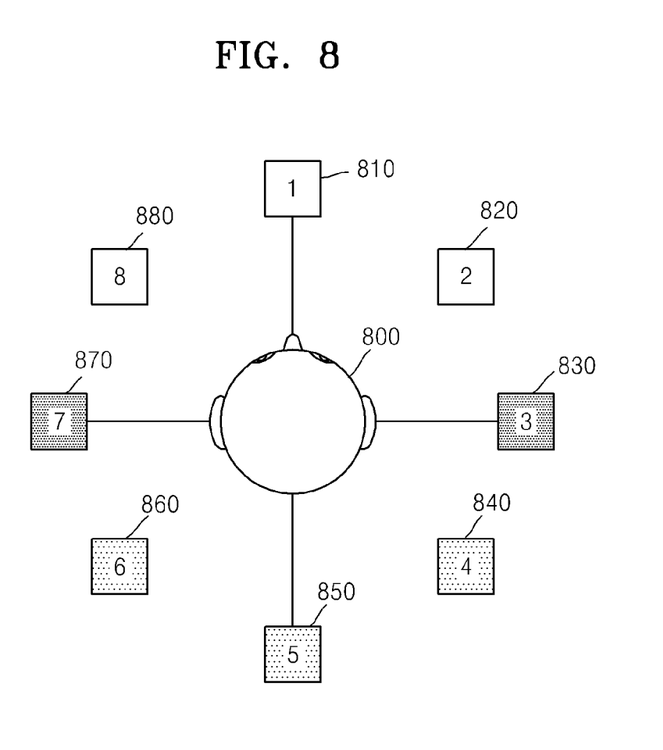
FIG. 8 is a diagram illustrating an example of testing a directivity of a hearing ability of a user in a multimedia playing apparatus.

FIG. 8 is a diagram illustrating an example of testing a directivity of a hearing ability of a user in a multimedia playing apparatus. Referring to FIG. 8, a sound is output from one of eight locations around a user 800. Thus, the sound is output from one direction toward the user 800. Each of numbers 1 through 8 denotes a location of outputting a sound, and may be a channel of the sound output unit 110 of FIG. 1. Hereinafter, for convenience of description, the numbers 1 through 8 will be referred to as channels 810 through 880, respectively. Each of the channels 810 through 880 is located at a predetermined distance from the user 800 to output a sound of a predetermined intensity. For example, each of the channels 810 through 880 may be located 1 m apart from the user 800.

In order to test the directivity of the hearing ability of the user exactly, the channels 810 through 880 are separated from each other at predetermined angles. For example, each of the channels 810 through 880 may be located at an angle of 45° from another channel. Accordingly, if the first channel 810 is located at a reference position of 0°, the second channel 820, the third channel 830, the fourth channel 840, the fifth channel 850, the sixth channel 860, the seventh channel 870, and the eighth channel 880 are located at angles of 45°, 90°, 135°, 180°, 225°, 270°, and 315°, respectively, from the first channel 810.

The multimedia playing apparatus 100 of FIG. 1 or 2 outputs the sound through one of the eight channels 810 through 880. When the sound is output from one channel, the user inputs a recognized direction of the sound through the user interface 120 of FIG. 1 or 2. For example, if the multimedia playing apparatus 100 outputs the sound through the fourth channel 840, the user may select one of the numbers 1 through 8 through the user interface 120.

When a user response is input into the user interface 120, the processor 130 of FIG. 1 or 2 compares a direction of the output sound with a direction input by the user. The processor 130 tests the directivity of the hearing ability of the user based on a result of the comparison. If the processor 130 determines that the user has a problem in recognizing the direction of the output sound according to the result of the comparison, the processor 130 determines an output time difference of the output sound based on a result of the test of the directivity, thereby compensating for an ability of the user to recognize the direction of the output sound. In more detail, the processor 130 determines the output time difference between channels of the sound output unit 110 for each frequency band based on the result of the test of the directivity.

As described above, the multimedia playing apparatus 100 tests of the directivity of the hearing ability of the user based on the sound output from the channels of the sound output unit 110. The multimedia playing apparatus 100 may test the directivity of the user based on the 8 channels shown in FIG. 8; however, the multimedia playing apparatus 100 is not limited thereto.

The multimedia playing apparatus 100 tests whether the user recognizes the direction of the output sound. Also, the multimedia playing apparatus 100 adjusts the output time difference based on the result of the test of the directivity, and modulates and outputs the sound based on the output time difference to help the user to recognize the direction of the output sound. Since the multimedia playing apparatus 100 helps the user to recognize the direction of the output sound, the user may recognize the output sound with much less intensity than if the ability of the user to recognize the direction of the output sound is not compensated for. Thus, further degradation of a hearing loss of the user may be prevented. Also, the user may hear the output sound clearly in a noisy environment.

According to the teachings above, there is provided a multimedia playing apparatus that acquires hearing characteristics of a user based on a sound including one or more phonemes, thereby testing a hearing ability of the user quickly and conveniently. Also, when the hearing ability is tested, the multimedia playing apparatus may be calibrated quickly and easily, and thus, the multimedia playing apparatus may acquire more accurate hearing characteristics of the user. Also, the multimedia playing apparatus plays multimedia with sound modulated according to the acquired hearing characteristics of the user, and thus, the user may listen to the multimedia without using a hearing aid. Further, the multimedia playing apparatus compensates a hearing loss of the user that includes a hearing loss in at least one ear by outputting the sound modulated with respect to each output channel.

The units described herein may be implemented using hardware components and software components. For example, the hardware components may include microphones, amplifiers, band-pass filters, audio to digital converters, and processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, that independently or collectively instructs or configures the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more computer readable recording mediums. The computer readable recording medium may include any data storage device that can store data which can be thereafter read by a computer system or processing device. Examples of the computer readable recording medium include read-only memory (ROM), random-access memory (RAM), CD-ROMs, magnetic tapes, floppy disks, optical data storage devices. Also, functional programs, codes, and code segments that accomplish the examples disclosed herein can be easily construed by programmers skilled in the art to which the examples pertain based on and using the flow diagrams and block diagrams of the figures and their corresponding descriptions as provided herein.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A multimedia playing apparatus comprising:
    a sound output unit configured to output a sound comprising one or more phonemes;
    a user interface configured to receive a user response to the phonemes; and
    a processor configured to
        acquire hearing characteristics of a user based on the user response, and
        determine an output level and an output time of the sound for each of frequency bands based on the hearing characteristics of the user,
    wherein
    the sound output unit is further configured to output the sound according to the output level and the output time of the sound for each of the frequency bands,
    the sound output unit comprises two or more channels,
    the processor is further configured to
        acquire hearing characteristics of a right ear and a left ear, respectively, based on the user response,
        determine the output level of the sound for each of the frequency bands for each of the channels based on the respective hearing characteristics of the right ear and the left ear,
        compare the hearing characteristics of the right ear and the left ear with each other, and
        determine an output level difference and an output time difference between the channels for each of the frequency bands based on a result of the comparison, and
    the sound output unit is further configured to output the sound according to the output level difference and the output time difference between the channels for each of the frequency bands.

2. The multimedia playing apparatus of claim 1, wherein:
    the sound output is further configured to output the sound toward the user from a direction through one or more of the channels;
    the user response comprises a direction of the sound that is input by the user; and
    the processor is further configured to compare the direction of the output sound and the direction of the sound that is input by the user to determine whether the user recognizes the direction of the output sound.

3. The multimedia playing apparatus of claim 2, wherein the processor is further configured to:
    determine an output time difference between the channels for each of the frequency bands based on whether the user recognizes the direction of the output sound.

4. The multimedia playing apparatus of claim 1, wherein:
    each of the hearing characteristics of the right ear and the left ear comprise a hearing threshold of a corresponding ear for each of the frequency bands; and
    the processor is further configured to
        determine a frequency band comprising the hearing threshold exceeding a predetermined permissible range based on the hearing characteristics of the right ear and the left ear, and
        compare the hearing characteristics of the right ear and the left ear with each other at the frequency band.

5. The multimedia playing apparatus of claim 4, wherein the processor is further configured to:
    increase the output level difference between the channels for a high frequency band if the frequency band is a low frequency band.

6. The multimedia playing apparatus of claim 4, wherein the processor is further configured to:
    increase the output time difference between the channels for a low frequency band if the frequency band is a high frequency band.

7. The multimedia playing apparatus of claim 1, wherein:
    the user interface comprises a sound level meter configured to measure a sound pressure of the sound;
    the processor is further configured to calibrate the sound pressure of the sound based on the measured sound pressure; and the sound output unit is further configured to output the sound according to the calibrated sound pressure.

8. The multimedia playing apparatus of claim 1, further comprising:
a memory configured to store the hearing characteristics of the user, and the output level of the sound for each of the frequency bands.

9. The multimedia playing apparatus of claim 1, further comprising:
a memory configured to store a history of hearing characteristics of each user,
wherein the processor is further configured to acquire the hearing characteristics of the user based on the history of the hearing characteristics of the user.

10. The multimedia playing apparatus of claim 1, wherein:
the processor is further configured to acquire a hearing threshold of the user for the phonemes; and
the hearing characteristics of the user comprise a hearing threshold of the user for each of the frequency bands corresponding to the phonemes.

11. The multimedia playing apparatus of claim 1, further comprising:
a memory configured to store groups of phonemes, the phonemes being classified into the groups based on peak frequencies of the phonemes.

12. A method of outputting a sound according to hearing characteristics of a user in a multimedia playing apparatus, the method comprising:
outputting a sound comprising one or more phonemes;
receiving a user response to the phonemes;
acquiring, at a processing device and with respect to a medical reference range determining normality of hearing ability, the hearing characteristics of the user based on the user response;
determining, at the processing device, an output level and an output time of the sound for each of frequency bands based on the hearing characteristics of the user;
outputting the sound according to the output level and the output time of the sound for each of the frequency bands so as to compensate loss of normality of hearing of the user;
outputting the sound through two or more channels;
acquiring hearing characteristics of a right ear and a left ear, respectively, based on the user response;
determining the output level of the sound for each of the frequency bands for each of the channels based on the respective hearing characteristics of the right ear and the left ear;
comparing the hearing characteristics of the right ear and the left ear with each other;
determining an output level difference and an output time difference between the channels for each of the frequency bands based on a result of the comparison; and
outputting the sound according to the output level difference and the output time difference between the channels for each of the frequency bands.

13. The method of claim 12, wherein:
each of the hearing characteristics of the right ear and the left ear comprise a hearing threshold of a corresponding ear for each of the frequency bands; and
the method further comprises
determining a frequency band comprising the hearing threshold exceeding the medical reference range based on the hearing characteristics of the right ear and the left ear, and
comparing the hearing characteristics of the right ear and the left ear with each other at the frequency band.

14. The method of claim 12, further comprising
measuring a sound pressure of the sound;
calibrating the sound pressure of the sound based on the measured sound pressure; and
outputting the sound according to the calibrated sound pressure.

15. The method of claim 12, further comprising:
acquiring a hearing threshold of the user for the phonemes,
wherein the hearing characteristics of the user comprise a hearing threshold of the user for each of the frequency bands corresponding to the phonemes.

16. A non-transitory computer-readable storage medium storing a program comprising instructions to cause a computer to perform the method of claim 12.

17. The method of claim 12, further comprising:
outputting the sound toward the user from a direction through one or more channels of the multimedia playing apparatus;
receiving the user response comprising a direction of the sound that is input by the user; and
comparing the direction of the output sound and the direction of the sound that is input by the user to determine whether the user recognizes the direction of the output sound.

18. The method of claim 17, further comprising:
determining an output time difference between the channels for each of frequency bands based on whether the user recognizes the direction of the output sound; and
outputting the sound according to the output time difference between the channels for each of the frequency bands.

* * * * *